United States Patent [19]

Thizy et al.

[11] 4,295,877
[45] Oct. 20, 1981

[54] SELECTIVE HERBICIDAL METHOD IN COTTON AND SOYBEANS

[75] Inventors: André Thizy; Pierre Poignant; Daniel Pillon, all of Lyons, France

[73] Assignee: Philagro, Lyons, France

[21] Appl. No.: 969,003

[22] Filed: Dec. 13, 1978

Related U.S. Application Data

[63] Continuation of Ser. No. 809,903, Jun. 24, 1977, abandoned, which is a continuation-in-part of Ser. No. 162,643, Jul. 14, 1971, abandoned.

[51] Int. Cl.³ ............................................. A01N 47/30
[52] U.S. Cl. ..................................................... 71/120
[58] Field of Search .......................................... 71/120

[56] References Cited

U.S. PATENT DOCUMENTS

| 3,649,241 | 3/1972 | Fitzgerald et al. | 71/120 |
| 3,779,738 | 12/1973 | Pillon et al. | 71/120 |

FOREIGN PATENT DOCUMENTS

| 2001791 | 10/1969 | France | 71/120 |

Primary Examiner—Catherine L. Mills

[57] ABSTRACT

The pre-emergence or post-emergence treatment for weed control in dicotyledonous crops with N-(4-isopropylphenyl)-N',N' dimethylurea and method for crop treatment.

8 Claims, No Drawings

SELECTIVE HERBICIDAL METHOD IN COTTON AND SOYBEANS

This is a continuation of application Ser. No. 809,903, filed June 24, 1977, abandoned which is in turn a continuation-in-part of application Ser. No. 162,643, filed on July 14, 1971, abandond.

This invention relates to the application of N-(4-isopropyl-phenyl)-N',N' dimethylurea having the formula:

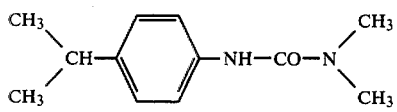

to weed control of dicotyledonous crops such as soybeans and cotton.

Some dimethylphenylureas have been used for some time against noxious plants. In practice, examples are:
N-(3,4-dichloro-phenyl)-N',N'dimethylurea (Diuron)
N-(4-chloro-phenyl)-N',N'dimethylurea (Monuron)
N-(3,4-dichloro-phenyl)-N'methyl, N'butyl urea (Neburon)
which are commonly used for crop weed control. The first two products have comparatively poor selective properties and cannot, in any event, be used for the control of adventitious plants present among cereals. On the other hand, Neburon has selective properties, and is widely used for cleaning cereal crops, particularly wheat.

It has been demonstrated that N-(4-isopropyl-phenyl)-N',N'dimethylurea (hereinafter mentioned as I.P.U.) has an overall activity comparable to and often higher than that of the most active above-mentioned ureas, while having an outstanding selectivity towards dicotyledonous crops, notably cotton and soya (soybeans).

The herbicidal properties of the compound I.P.U. is mentioned in U.S. Pat. No. 2,655,447 among a large number of other phenylureas. The herbicidal activity of some of the described phenylureas is demonstrated on only two bush plants. *Agropyrum repens* and *Sorghum halepense*. The herbicidal activity of I.P.U. on the adventitious plants present among cotton and soy beans and the selectivity thereof towards the latter, are not mentioned. Moreover, in the above-cited patent, only the formula of I.P.U. is indicated, while neither the physico-chemical features nor the biological properties thereof are mentioned.

First of all, we have provided the synthesis of the said substance, and have shown that the phenylureas described in the above-mentioned U.S. patent, which, according to the indications therein, all seem to have the same properties, cannot all be applied to the selective destruction of adventitious plants present in dicotyledonous crops, notably cotton and soy beans, because either they lack herbicial activity, or their activity is too marked towards the crop itself. I.P.U. is definitely different from its homologs, as will be shown by the following examples.

The compound I.P.U. can be produced by allowing p-isopropylphenyl isocyanate to react with dimethylamine in benzene solution. The isocyanate may be prepared by any of the following processes: acylation of cumene, and oxidation of the p-isopropylacetophenone thus obtained, followed by cyanation of the resulting chloride of p-isopropyl benzoyl; or by nitration of cumene, followed by catalytic reduction and action of phosgene on the resulting p-isopropylaniline.

EXAMPLE 1: Synthesis of I.P.U.

Dimethylamine (0.1 mole) dissolved in 25 ml of anhydrous benzene is introduced into a flask containing 0.04 mole of p-isopropylphenylisocyanate dissolved in 100 ml of anhydrous benzene. The reaction mixture is then boiled for one hour. On cooling, the urea precipitates out as white crystals, which are washed and vacuum dried. Reaction yield: 92%. The melting point of the resulting crystals is 157° C., and analysis gives the following results:

|  | C, % | H, % | N, % |
|---|---|---|---|
| Calculated | 69.90 | 8.73 | 13.59 |
| Found | 69.64 | 9.18 | 13.62 |

The selective herbicidal properties of I.P.U. have been demonstrated by various tests, wherein the said product has been compared with its homologs. The tests were carried out as follows:

Pots (10×10×15 cm) were filled with earth which had never been subjected to herbicidal treatment. Seeds of various species of plants of which the sensitivity to the herbicides is to be tested, were placed on the earth. The seeds are then covered with a layer of earth, the depth of which depends on the diameters of the seeds. The herbicidal composition consists of a wettable powder prepared by mixing the following ingredients for one minute in a cutter-mill:

| | |
|---|---|
| Active material to be tested | 20% |
| Defloculating agent (calcium lignosulfate) | 5% |
| Wetting agent (sodium alkarylsulfonate) | 1% |
| Carrier (alumina silicate) | 74% |

This wettable powder is then mixed with a quantity of water calculated to give the required level per hectare by a spraying operation.

In every test, an untreated control plant is used, so as to enable a check on possible growth inhibition, and also a possible lack of germination, or defective growth of the plants due to particular conditions.

The pots treated in this way are then kept for some time in a greenhouse under constantly controlled moisture, temperature and lighting conditions. At the end of five weeks, the results are noted, in particular by estimating the percentage of destruction of each species with respect to the reference plant. It is understood that with reference to post-emergence, the spraying operation is carried out after the plants have germinated and reached the 2-leaf stage.

The various crops and adventitious plants on which tests were carried out are as follows:

| Species | Scientific name | Symbol |
|---|---|---|
| Wild oats | *Avena fatua* | AV |
| Wheat | *Triticum vulgare* | BL |
| Maize | *Zea mays* | MA |
| Barnyard grass | *Echinochloa crus galli* | PA |
| Rice | *Oryza sativa* | RI |
| Rye grass | *Lolium italicum* | RA |

-continued

| Act. Mat. | Amount ha | SO | CO | AV | RA | PA | VU | AM | CH | MO | SA |
|---|---|---|---|---|---|---|---|---|---|---|---|
| I.P.U. | 2 kg | 0 | 10 | 100 | 100 | 100 | 100 | 100 | 100 | 98 | 100 |
|  | 1 kg | 0 | 0 | 100 | 98 | 100 | 100 | 98 | 100 | 98 | 100 |
|  | 0.5 kg | 0 | 0 | 98 | 95 | 100 | 90 | 98 | 85 | 95 | 98 |
| A | 4 kg | 100 | 20 | 100 | 100 | 100 | 100 | 100 | 100 | 98 | 100 |
|  | 2 kg | 99 | 0 | 100 | 100 | 100 | 100 | 100 | 100 | 96 | 100 |
|  | 1 kg | 99 | 0 | 100 | 100 | 100 | 100 | 100 | 100 | 90 | 100 |
| B | 4 kg | 100 | 60 | 100 | 100 | 100 | 100 | 100 | 100 | 99 | 100 |
|  | 2 kg | 100 | 10 | 100 | 100 | 100 | 100 | 100 | 100 | 85 | 100 |
|  | 1 kg | 95 | 0 | 100 | 100 | 100 | 100 | 100 | 100 | 70 | 100 |
|  | 4 kg | 40 | 98 | 2 | 50 | 60 | 85 | 99 | 100 | 97 | 100 |
| E | 2 kg | 10 | 95 | 0 | 40 | 50 | 25 | 95 | 99 | 85 | 70 |
| F | 2 kg | 0 | 55 | 0 | 15 | 65 | 0 | 98 | 97 | 95 | 96 |

| Species | Scientific name | Symbol |
|---|---|---|
| Foxtail grass | *Alopecurus myosuroides* | VU |
| Amaranth | *Amaranthus retroflexus* | AM |
| Lambs' quarter | *Chenopodium album* | CH |
| White mustard | *Sinapis alba* | MO |
| Buckwheat | *Polygonum fagopyrum* | SA |
| Cotton | *Gossypium hirsutum* | CO |
| Soybean | Glycine wax | SO |

In each test, I.P.U. was compared with certain of the ureas described in U.S. Pat. No. 2,655,447, as well as with the best known herbicidal ureas now commercially available.

EXAMPLE 2: PRE-EMERGENCE TRIALS

The results obtained are shown in the following table, wherein the destruction percentages on species for each compound tested are indicated. The active materials are identified by the following symbols:

| Active material | Symbol |
|---|---|
| Isopropyl phenyl dimethylurea | I.P.U. |
| Diuron | A |
| Monuron | B |
| Neburon | C |
| N-(3,4-dichlorophenyl) N' methylurea | D |
| N-(4-methoxyphenyl) N' N' dimethylurea | E |
| N-(isopropoxyphenyl) N' N' dimethylurea | F |

| Act. Mat. | Amount ha | SO | CO | AV | RA | PA | VU | AM | CH | MO | SA |
|---|---|---|---|---|---|---|---|---|---|---|---|
| I.P.U. | 4 kg | 0 | 40 | 100 | 100 | 100 | 100 | 100 | 100 | 100 | 100 |
|  | 2 kg | 0 | 0 | 100 | 100 | 100 | 100 | 100 | 100 | 100 | 100 |
|  | 1 kg | 0 | 0 | 100 | 98 | 98 | 98 | 98 | 100 | 98 | 100 |
|  | 0.5 kg | 0 | 0 | 98 | 90 | 95 | 50 | 98 | 100 | 70 | 75 |
| A | 4 kg | 100 | 98 | 100 | 100 | 100 | — | — | 100 | 100 | 100 |
|  | 2 kg | 100 | 20 | 98 | 100 | 100 | — | — | 100 | 100 | 100 |
|  | 1 kg | 98 | 10 | 60 | 98 | 98 | — | — | 100 | 98 | 85 |
| B | 4 kg | 100 | 80 | 100 | 100 | 100 | — | — | 100 | 100 | 100 |
|  | 2 kg | 100 | 80 | 100 | 100 | 100 | — | — | 100 | 100 | 100 |
|  | 1 kg | 95 | 10 | 98 | 98 | 100 | — | — | 100 | 100 | 95 |
| C | 4 kg | 10 | 0 | 0 | 0 | 95 | 25 | 100 | 100 | 100 | 98 |
|  | 2 kg | 0 | 0 | 0 | 0 | 75 | 10 | 98 | 98 | 98 | 95 |
| D | 4 kg | 100 | 0 | 100 | 100 | 100 | 100 | 100 | 100 | 100 | 100 |
|  | 2 kg | 100 | 0 | 98 | 100 | 100 | 75 | 100 | 100 | 100 | 95 |
| E | 4 kg | 90 | 60 | 30 | 55 | 10 | 50 | 95 | 90 | 90 | 100 |
|  | 2 kg | 20 | 0 | 10 | 10 | 0 | 20 | 90 | 80 | 70 | 85 |
|  | 1 kg | 20 | 0 | 0 | 5 | 0 | 10 | 0 | 80 | 25 | 60 |
| F | 8 kg | 0 | 90 | 15 | 5 | 88 | 10 | 97 | 100 | 98 | 95 |
|  | 2 kg | 0 | 80 | 0 | 0 | 0 | 0 | 85 | 100 | 25 | 5 |

EXAMPLE 3: POST-EMERGENCE TRIALS

The results obtained are given in the following table, wherein the destruction percentages by species for each compound tested are indicated. The active materials are identified by the same symbols as in the preceding table.

EXAMPLE 4: OPEN-AIR TRIALS

During winter and spring 1970-1971, I.P.U. formed the subject of numerous field tests. These tests were intended as confirmation of its ability for use under practical conditions including factors, such as the nature of the ground and atmospheric conditions which often significantly modify the results obtained and are not taken into account in greenhouse tests.

The tests were carried out on 20 square meter plots, both for pre- and post-emergence, using a wettable powder formulated as follows:

| I.P.U. | 50% |
|---|---|
| Wetting agent (alkylnaphthalenesulfone) | 1% |
| Defloculating agent (lignosulfite) | 5% |
| Carrier (silica + china clay) | 44% | and diluted in a sufficient amount of water to give the desired quantity per hectare of active material, the efficiency of which is to be ascertained.

I.P.U. is advantageous in that its activity is always at least equal to that of the most active ureas, while its selectivity is at least equal to that of Neburon. If I.P.U. is compared more particularly with Neburon, it will be seen that I.P.U. has a much better activity on adventitious plants found very frequently among dicotyledonous crops, notably cotton and soybeans, rye grass, wild oats, barnyard grass and black grass.

I.P.U. is effective when used both pre- and post-emergence. In resume, it differs from the previously known ureas in that it has an outstanding selectivity towards some dicotyledonous crops, such as cotton and soybeans, besides which it has a very good activity on most of the adventitious plants present in said crops. Under the same conditions, the ureas heretofore reported are either highly herbicidal but not selective enough on said crops, or insufficiently active on weeds.

In practice, I.P.U. is effective when used in amounts ranging from 0.2 to 5 kg/ha, depending on the nature of the treatment to be carried out, and the varieties and the growth of the adventitious plants. While amounts greater than 5 kg/ha can be used, the increase in effect is not compensated by the cost.

In general, I.P.U. will be formulated according to the conventional methods used in the herbicide industry. The purpose of the formulation of the active materials is to provide easily used compositions with maximum activity on the weeds to be destroyed. To this end, in general, a number of carriers and additives, depending on the type of formulation contemplated and the result described, are added to the pure active material. The compositions thus obtained are either in liquid form (emulsions, true solutions, pastes, suspensions, and the like) ready to be used or to be diluted with water, or in solid form (wettable powders, granules, and the like) to be used as such or to be diluted in a liquid medium before use.

Such compositions include carriers, generally inert, and/or organic, mineral, or mixed solvents, and/or emulsifying agents, adhesive agents, anti-caking agents, defloculating agents, and the like.

In particular, data concerning formulations may be found in Fryer and Evans "Weed Control Handbook", 5th edition, p. 101 and following.

We claim:

1. A method for weed control in dicotyledonous crops comprising pre-emergence and post-emergence application of a herbicidally effective amount of N-(4-isopropylphenyl)-N',N'-dimethylurea to a dicotyledonous crop selected from the group consisting of soybeans and cotton.

2. The method as claimed in claim 1 in which the compound is applied in an amount of at least 0.2 kg per hectare.

3. The method as claimed in claim 1 in which the compound is applied in an amount within the range of 0.2 to 5 kg per hectare.

4. The method as claimed in claim 1 in which the compound is formulated into a composition which includes a carrier and other additives.

5. The method as claimed in claim 4 in which the carrier is an inert liquid.

6. The method as claimed in claim 4 in which the additives include emulsifying agents, adhesive agents, anticaking agents, defloculating agents and filler.

7. The method for weed control in soybeans comprising pre-emergence or post-emergence application of a herbicidally effective amount of N-(4-isopropylphenyl)-N',N'-dimethylurea to soybeans.

8. The method for weed control in cotton comprising pre-emergence or post-emergence application of a herbicidally effective amount of N-(4-isopropylphenyl)-N',N'-dimethylurea to cotton.

* * * * *